(12) United States Patent
Petrella et al.

(10) Patent No.: US 7,275,218 B2
(45) Date of Patent: Sep. 25, 2007

(54) METHOD, APPARATUS, AND PROGRAM FOR ANALYZING A PROSTHETIC DEVICE

(75) Inventors: Anthony J. Petrella, Ft. Wayne, IN (US); Paul R. Tomaszewski, Columbia City, IN (US)

(73) Assignee: DePuy Products, Inc., Warsaw, IN (US)

( * ) Notice: Subject to any disclaimer, the term of this patent is extended or adjusted under 35 U.S.C. 154(b) by 842 days.

(21) Appl. No.: 10/112,781

(22) Filed: Mar. 29, 2002

(65) Prior Publication Data
US 2003/0184577 A1 Oct. 2, 2003

(51) Int. Cl.
G06F 3/00 (2006.01)

(52) U.S. Cl. .................. 715/771; 715/843; 715/738; 715/745; 715/964; 703/7; 623/914

(58) Field of Classification Search .............. 623/914; 715/964, 843, 841, 771; 703/7
See application file for complete search history.

(56) References Cited

U.S. PATENT DOCUMENTS

| | | | | |
|---|---|---|---|---|
| 5,297,057 | A * | 3/1994 | Kramer et al. .................. | 703/7 |
| 5,450,540 | A * | 9/1995 | Spohrer et al. ............. | 715/763 |
| 5,539,649 | A * | 7/1996 | Walsh et al. ................ | 700/163 |
| 5,689,668 | A * | 11/1997 | Beaudet et al. ............. | 715/841 |
| 5,880,964 | A * | 3/1999 | Schall et al. ................ | 700/159 |
| 5,880,976 | A * | 3/1999 | DiGioia, III et al. ........... | 703/7 |
| 5,995,738 | A | 11/1999 | DiGioia, III et al. | |
| 6,002,859 | A | 12/1999 | DiGioia, III et al. | |
| 6,141,463 | A * | 10/2000 | Covell et al. ................ | 382/286 |
| 6,205,411 | B1 | 3/2001 | DiGioia, III et al. | |
| 6,377,281 | B1 * | 4/2002 | Rosenbluth et al. ........ | 715/700 |

OTHER PUBLICATIONS

Sadoski, Client/Server Software Architectures—An Overview Dec. 6, 1998, Carnegie Mellon University, pp. 1-6.*
"The Effect of Component Postion on Motion to Impingement and Dislocation in Total Hip Replacement", C.Lavernia et al. (5 Pages), a scientific exhibit at the AAOS metting, New Orleans, Louisiana.*
"The Effects of Neck Geometry and Acetabular Design on the Motion to Impingement in Total Hip Replacement", C. Thornberry et al., (5 pages) , a scientific exhibit at the AAOS metting, New Orleans, Louisiana.*

(Continued)

Primary Examiner—Kristine Kincaid
Assistant Examiner—Ryan Pitaro
(74) Attorney, Agent, or Firm—Barnes & Thornburg LLP

(57) ABSTRACT

A method for analyzing a prosthetic device includes the step of displaying a graphical user interface. The method further includes determining a user selected prosthetic device via the graphical user interface. The method also includes determining a first user selected orientation for the prosthetic device via the graphical user interface. Moreover, the method includes displaying an image of the prosthetic device via the graphical user interface. The method yet further includes calculating a first data set indicative of a first range of motion for the prosthetic device orientated in the first user selected orientation, and displaying a graphical representation of the first data set via the graphical user interface. An apparatus for analyzing a prosthetic device is also disclosed.

34 Claims, 15 Drawing Sheets

OTHER PUBLICATIONS

"The Effect of Component Position on Motion to Impingement and Dislocation In Total Hip Replacement", C. Lavernia et al. (5 pages), a scientific exhibit at the 1998 AAOS meeting, New Orleans, Louisiana.

"The Effects of Neck Geometry and Acetabular Design on the Motion to Impingement in Total Hip Replacement", C. Thornberry et al., (5 pages), a scientific exhibit at the 1998 AAOS meeting, New Orleans, Louisiana.

CD-ROM "Range of Motion Analysis", Interface 1.0, Smith & Nephew, disclosed at a tradeshow in 1998 with installation and installing instructions (2 pages).

S. Mattessich et al., "Effects of Femoral Head Design, Cup Orientation, and Wear on Hip Range of Motion", 46th Annual Meeting, Orthopaedic Research Society, Mar. 12-15, 2000, 1 pg.

B. Jaramaz et al., "Sensitivity of Impingement Limits to Error in Cup Placement", 44th Annual Meeting, Orthopaedic Research Society, Mar. 16-19, 1998, 1 pg.

B. Jaramaz et al., "Effect of Cup Orientation and Neck Length in Range of Motion Simulation", 43rd Annual Meeting, Orthopaedic Research Society, Feb. 9-13, 1997, 1 pg.

C. F. Scifert et al., "Direct Physical Validation of a Finite Element Model of Total Hip Dislocation", 44th Annual Meeting, Orthopaedic Research Society, Mar. 16-19, 1998, 1 pg.

D. D. D'Lima, M.D. et al., "The Effect of the Orientation of the Acetabular and Femoral Components on the Range of Motion of the Hip at Different Head-Neck Ratios", The Journal of Bone and Joint Surgery, 2000, pp. 315-321.

J. Lipman et al., "The Effect of Highwall Liner Orientation on Total Hip Range-of-Motion During Activities of Daily Living", 47th Annual Meeting, Orthopaedic Research Society, Feb. 25-28, 2001, 1 pg.

D. DiLima et al., "Acetabular Component Position Affects Contact Stresses: A Nonlinear Viscoelastic Finite Element Model", 46th Annual Meeting, Orthopaedic Research Society, Mar. 12-15, 2000, 1 pg.

B. Jaramaz et al., "Effect of Cup Orientation and Neck Length in Range of Motion Simulation", Source and Date Unknown, 2 pgs.

P. L. Cheng et al., "Graphical presentation of the range of hip and knee rotations for clinical evaluation of gait", Clinical Biomechanics 16, 2001, pp. 84-86.

B. Jaramaz et al., "Range of Motion After Total Hip Arthroplasty: Experimental Verification of the Analytical Simulator", Shadyside Hospital and Carnegie Mellon University, Feb. 20, 1997, 14 pgs.

* cited by examiner

METHOD, APPARATUS, AND PROGRAM FOR ANALYZING A PROSTHETIC DEVICE

TECHNICAL FIELD OF THE DISCLOSURE

The present invention relates generally to analysis software, and more particularly to a method, apparatus, and program for analyzing a prosthetic device.

BACKGROUND

Determination of the range of motion of a prosthetic joint implant is essential to insure that impingement between one or more of the components of the implant and/or bone does not occur. Techniques for determining the range of motion of joint implants using a simulation model in a computer are known in the art. For example, it is known to construct a computer graphic model of the pelvis and femur from CT data using contouring and triangulation mesh algorithms. As such, this technique requires a "custom" model which is specific to each individual patient. These custom models are then incorporated into computer software which models the hip as a ball-and-socket joint and calculates range of motion via a collision detection algorithm. Such heretofore utilized techniques, while useful in a laboratory setting, are somewhat cumbersome because such techniques require the user to create graphic models more or less by hand, and rewrite and/or recompile the software in order to analyze differing prosthetic combinations.

What is needed is a method, apparatus, and program that provide a quick and intuitive comparative assessment of range of motion for any general geometry and orientation of intact or replaced human joint. The method, apparatus, and program should allow for the analysis of the effects of prosthetic device component selection on the joint range of motion. The method, apparatus, and program should further allow for the analysis of the effects of alignment of the components on the joint range of motion.

SUMMARY

In accordance with one embodiment of the present disclosure, a method is provided for analyzing a prosthetic device. The method includes the step of displaying a graphical user interface. The method also includes determining a user selected prosthetic device via the graphical user interface. The method further includes determining a first user selected orientation for the prosthetic device via the graphical user interface. The method also includes displaying an image of the prosthetic device via the graphical user interface. Moreover, the method includes calculating a first data set indicative of a first range of motion for the prosthetic device orientated in the first user selected orientation. In addition, the method includes displaying a graphical representation of the first data set via the graphical user interface.

In accordance with another embodiment of the present disclosure, a method is provided for analyzing a prosthetic device. The method includes the step of displaying a graphical user interface on a first computer. The method also includes determining a user selected prosthetic device via the graphical user interface. The method further includes determining a user selected orientation for the prosthetic device via the graphical user interface. The method also includes displaying an image of the prosthetic device via the graphical user interface. Moreover, the method includes calculating a data set indicative of a first range of motion for the prosthetic device, the calculation based upon the user selected orientation for the prosthetic device, the calculation performed by a second computer. A graphical representation of the data set is displayed via the graphical user interface.

In accordance with another embodiment of the present disclosure, an apparatus is provided for analyzing a prosthetic device. The apparatus includes a display monitor and a processing unit electrically coupled to the display monitor. The apparatus also includes a memory electrically coupled to the processing unit. The memory has stored therein a plurality of instructions which, when executed by the processing unit, causes the processing unit to display a graphical user interface on the display monitor. The instructions also cause the processing unit to determine a user selected prosthetic device via the graphical user interface. A first user selected orientation for the prosthetic device is determined via the graphical user interface. The instructions also cause the processing unit to display an image of the prosthetic device on the display monitor via the graphical user interface. The instructions also cause the processing unit to calculate a first data set indicative of a first range of motion for the prosthetic device orientated in the first user selected orientation, and display a graphical representation of the first data set via the graphical user interface.

DETAILED DESCRIPTION OF THE DRAWINGS

Figure 1:
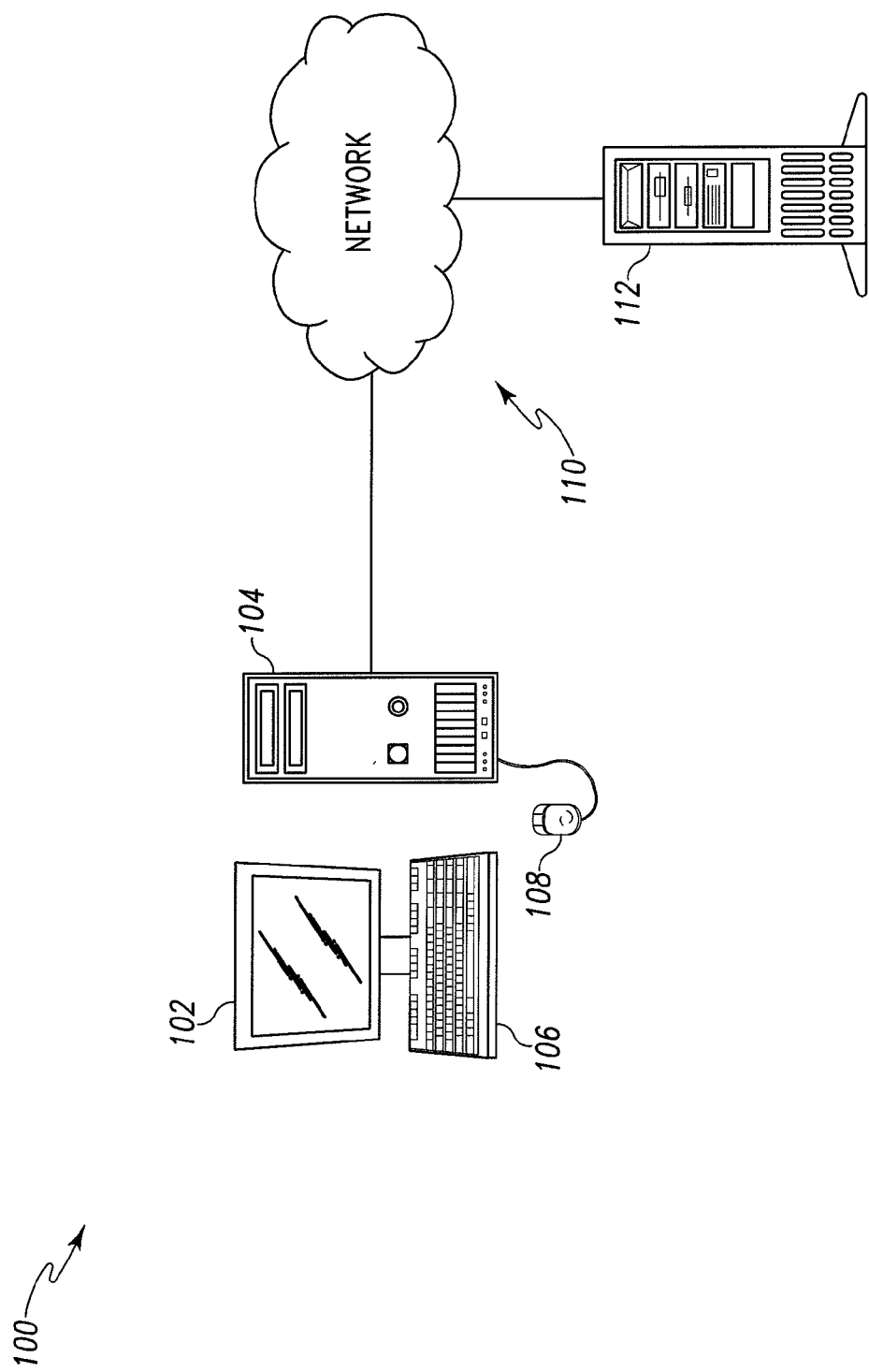
FIG. 1 is a simplified block diagram illustrating two embodiments of the present disclosure, the first being a stand-alone single computer system, the second being a network-based system.

While the disclosure is susceptible to various modifications and alternative forms, specific embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives falling within the spirit and scope of the disclosure as defined in the appended claims.

Referring now to FIG. 1, there is shown a computer system 100 for use in a home or a business. Computer system 100 includes monitor 102, central processing unit (CPU) 104, keyboard 106, and pointing device 108. In one illustrative embodiment, computer system 100 is a personal computer capable of running a graphical user interface (GUI) enabled operating system. Pointing device 108 could be, for example, a mouse, a track ball, a light pen, or any other known pointing device.

In one illustrative embodiment, computer system 100 is a stand-alone computer in which all system and application software is maintained in a memory and/or storage device associated therewith. In a second illustrative embodiment, computer system 100 is coupled to network 110. Network 110 could be any known type of network. For example, network 110 could be a wireless local area network (LAN), a wired LAN, a wide area network (WAN), a global network such as the Internet, or one or more computers coupled via a modem connection or a serial connection. In this embodiment, network 110 is further coupled to server computer 112. In this embodiment, some software to be executed by computer system 100 resides on server 112, while other software to be executed by computer system 100 is located on computer system 100.

Those skilled in the art will recognize that irrespective of where the software to be executed by computer system 100 is stored, the same general software algorithms will be performed. For example, in one exemplary embodiment, the graphical user interface for the software package will be executed by computer system 100, although the software to execute the graphical user interface will be stored on both computer system 100 and server 112. In another embodiment, the software to execute the graphical user interface will be stored on only computer system 100. In yet another embodiment, the software to execute the graphical user interface will be stored on only server 112. Likewise, in the network-based embodiment, mathematical calculations could be carried out on either computer system 100, file server 112, or some combination of the two. The exemplary embodiments described herein are not intended to limit the claimed invention in any way.

Figure 2:
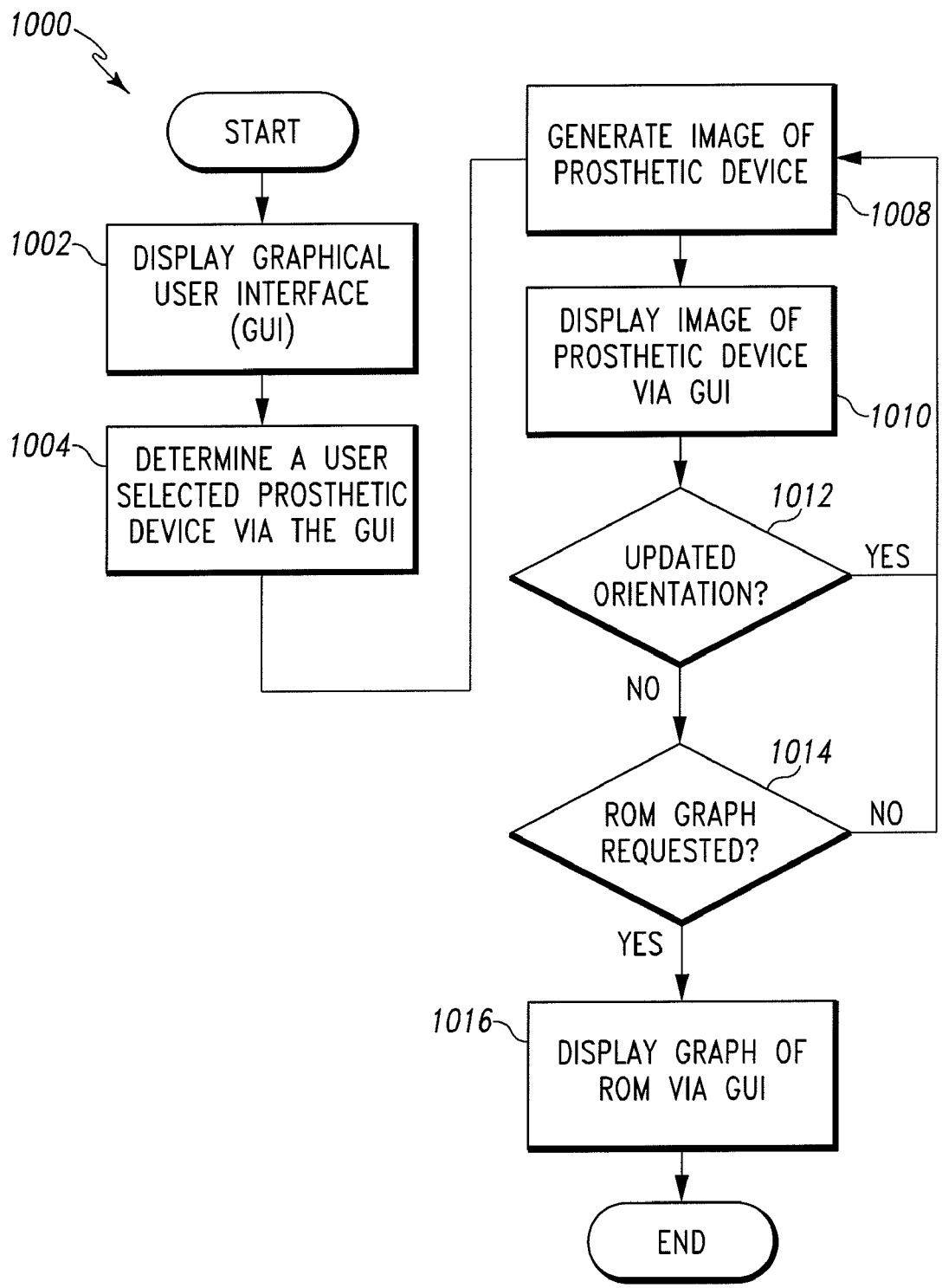
FIG. 2 is a flow chart of a general procedure for analyzing a prosthetic device.

Referring now to FIG. 2, there is shown a flow chart which sets forth a general procedure 1000 for analyzing and visualizing the range of motion of a prosthetic joint. The procedure 1000 starts at step 1002 in which a graphical user interface (GUI) is displayed on display monitor 102 of computer system 100. As will be discussed herein in greater detail, use of a graphical user interface provides a convenient manner of communicating information with the user. The procedure 1000 then advances to step 1004.

In step 1004, the procedure determines whether the user has selected a particular prosthetic device via the graphical user interface. In particular, a list of prosthetic devices may be displayed on the display monitor 102 for presentation to the user. In step 1004, the procedure determines which prosthetic device is selected from the list. The list may be tailored to include any number or type of prosthetic devices. For example, prosthetic hip devices, shoulder devices, knee devices, or the like may be included in the displayed list. Moreover, the displayed prosthetic devices may include any number of components. In particular, a number of different lists may be displayed, each of which includes a separate component associated with the prosthetic device. For example, a first list may include a number of different implantable acetabular cups, a second list may include a number of acetabular bearing inserts for use with an acetabular cup, a third list may include a number of prosthetic femoral stems, and a fourth list may include a number of prosthetic head components for use with a prosthetic femoral stem. Similar lists of shoulder components, knee components, etcetera may also be displayed based on the type of prosthetic device to be analyzed. In any event, in step 1004 the procedure determines when a user selects a prosthetic device from one of the displayed lists. The procedure 1000 then advances to step 1008.

In step 1008, the procedure generates an image of the user-selected prosthetic device that was selected from the displayed list or lists. This image is generated as a data set which represents an image such as a bit map data set. This image is generated to simulate a view of the selected prosthetic device positioned in either a user-selected orientation (described below in regard to step 1012) or in a default user-selected orientation. While this image is generated as a two-dimensional image, the data set from which the image is calculated represents a three-dimensional model of the prosthetic device thereby creating the illusion that the user is viewing a three-dimensional prosthetic device in three-dimensional space.

The procedure then advances to step 1010 in which the image generated in step 1008 is displayed on the display monitor 102 for presentation to the user via the graphical user interface. The image of the prosthetic device is generally displayed along with an image of the bone or bones into which the device is designed to be implanted. For example, in the case of a hip prosthetic device, the image of the prosthetic device is generally displayed along with an image of the pelvic bone and the femur. Similarly, the image of a shoulder prosthetic device is generally displayed along with an image of the scapula and the humerus. It should be appreciated that in the case of other types of prosthetic devices, an image of the bone structures into which such devices are implanted may likewise be displayed.

The procedure 1000 then advances to step 1012. In step 1012, the procedure determines, via the graphical user interface, whether the user has selected a particular orientation of the selected prosthetic device. In particular, once the user has the opportunity to view the prosthetic device (along with the corresponding bone structure), the user may desire to change the orientation of one or more of the components associated with the prosthetic device. To do so, a number of default orientation angles may be displayed on the display monitor 102 for presentation to the user. In step 1012, the procedure determines if user changes either a default value or a previously entered user-selected value for the various orientation angles of the prosthetic device. For example, a number of input fields may be displayed which allow the user to select, for example, an abduction angle associated with the prosthetic device, an anteversion angle associated with the prosthetic device, or a rotation angle associated with the prosthetic device. It should be appreciated that any number or types of input fields indicative of any number or type of degrees of freedom of the prosthetic device's orientation may be displayed. In any event, in step 1012 the procedure determines if a user adjusts the angle in which the prosthetic device is orientated in one or more directions. If the user does so (via the graphical user interface), the procedure loops back to step 1008 to generate and thereafter display an image of the prosthetic device positioned in its revised orientation. If the user does not update the orientation of the prosthetic device, the procedure advances to step 1014.

In step 1014, the procedure determines whether the user has requested a range of motion graph. In particular, the procedure determines if the user has requested a range of motion graph by entering such a request via the graphical user interface. If the user has not requested a range of motion graph, the procedure returns to step 1008 and continues in a loop routine until either (i) an update of the orientation of the prosthetic device has been entered, or (ii) a range of motion graph has been requested. However, if the procedure determines at step 1014 that the user has requested a range of motion graph, then the procedure advances to step 1016.

In step 1016, the procedure displays a graph of the range of motion which is indicative of the operative range of motion of the skeletal structures associated with the joints into which the selected prosthetic device is to be implanted.

The graph may be formatted in any desired manner. One illustrative range of motion graph includes two axes with the X-axis representing degrees of abduction in the negative direction and degrees of adduction in positive direction, and the Y-axis representing degrees of flexion in the positive direction and degrees of extension in the negative direction. The origin of such an illustrative graph is the joint containing the implanted prosthetic device. The range of motion plot in such a graph may be calculated as a series of points which are linked together by a series of line segments. A conventional collision algorithm is used to calculate the location of each of the series of points.

At the completion of step 1016, the procedure ends. At this point, the procedure awaits input from a user indicative of another analysis request at which point the procedure loops back to step 1002.

The aforedescribed procedure will now be described in greater detail in regard to a specific prosthetic device. In particular, the procedure of the present disclosure will now be illustratively described in regard to a hip prosthetic device having four components—a shell (or "cup" as it is often referred to), a liner (or "bearing insert" as it is often referred to), a femoral stem, and a femoral head. However, it should be appreciated that while the following discussion is particular to a hip prosthetic device, such discussion is merely exemplary in nature and that the procedure may be modified to analyze any type of prosthetic device having any number of components.

Figure 3:
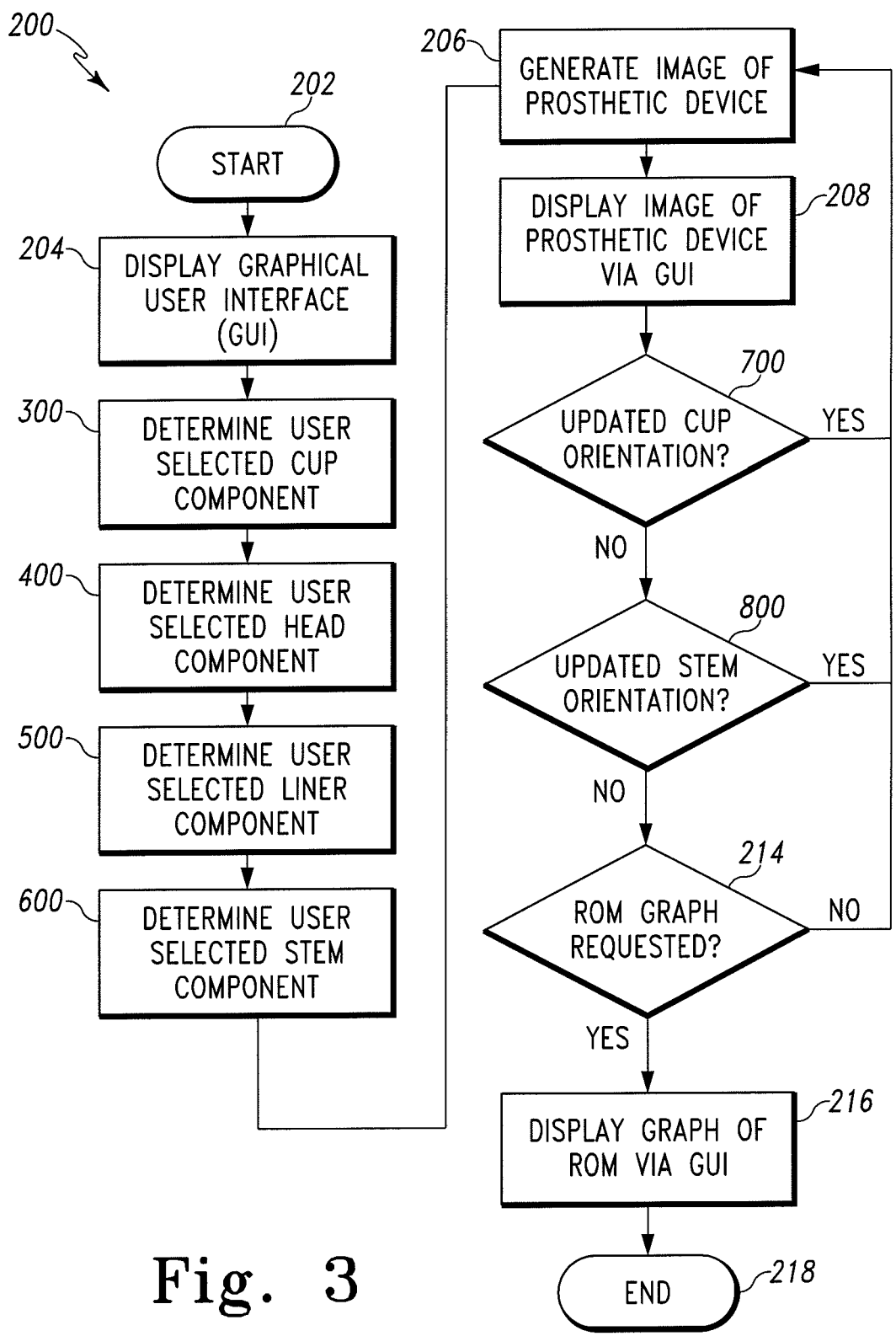
FIG. 3 is a flow chart of a specific implementation of the general procedure set forth in FIG. 2 for analyzing a hip prosthetic device.

In any event, referring now to FIG. 3, there is shown a flow chart which sets forth the general procedure 200 for the calculation and visualization of the range of motion of a hip joint having a prosthesis implanted therein. When the user activates the procedure at computer system 100, the procedure begins at step 202. The procedure advances to step 204, which causes a graphical user interface (GUI) to be displayed on monitor 102 of computer system 100.

Figure 10:
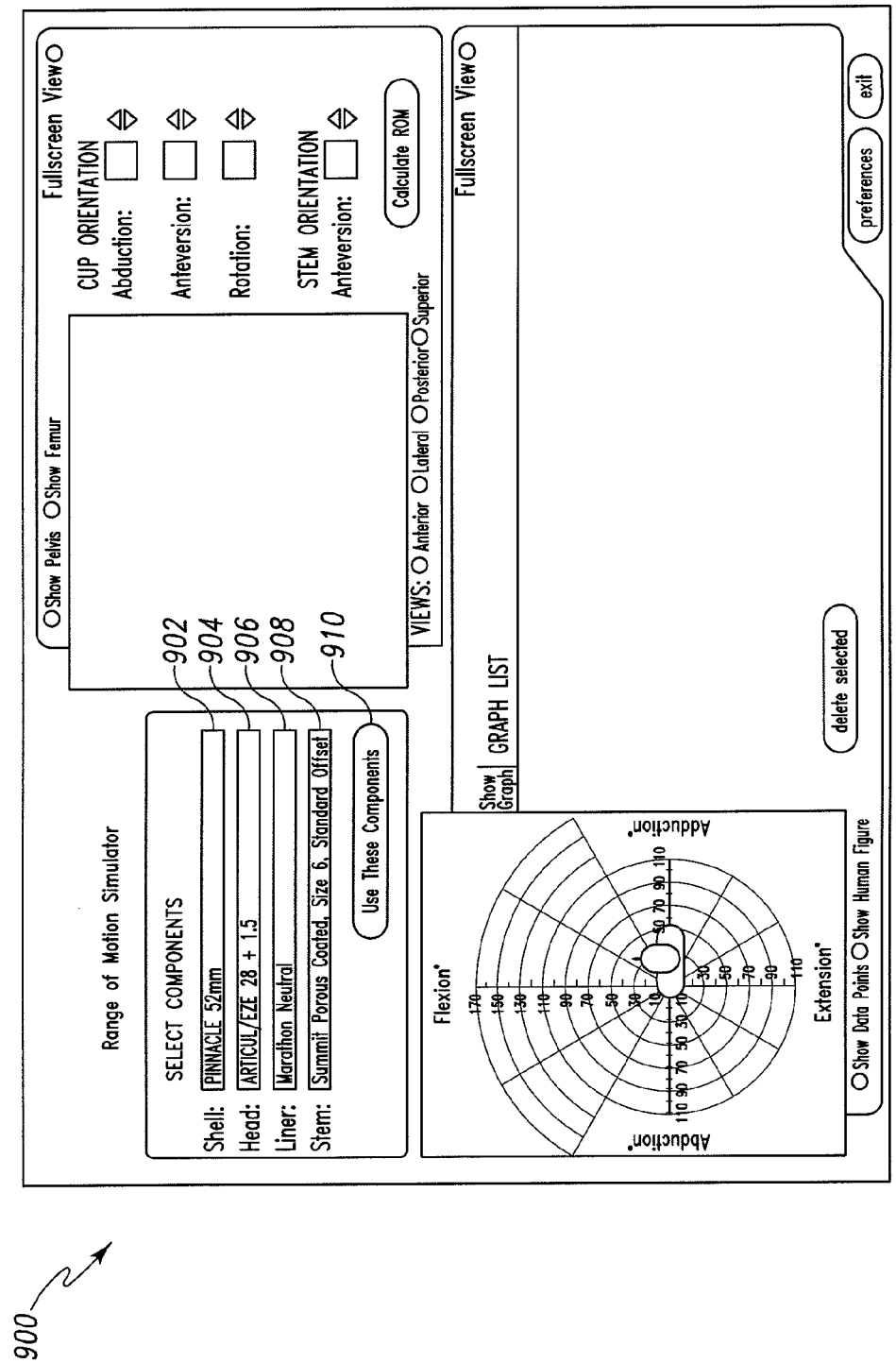
FIGS. 10-15 show various illustrative display screens which illustrate a graphical user interface for use with the procedure of FIG. 3.

An illustrative graphical user interface 900 is shown in FIG. 10. Graphical user interface 900 provides a convenient manner of communicating information with the user. Graphical user interface 900 could be implemented in Java produced by Sun Microsystems; Windows, produced by Microsoft Corp.; any of the various implementations of X-Windows; Shockwave, produced by Macromedia; Director, produced by Macromedia; MacOS, produced by Apple Computer Co.; or any other known programming or scripting language capable of creating a graphical user interface. Furthermore, graphical user interface 900 could be implemented software without the aid of an operating system or scripting language.

At the completion of step 204, procedure 200 advances to step 300, where a user selected acetabular cup component is determined. Step 300, which is actually a procedure, is described in greater detail below in reference to FIG. 4. Note that as used herein, the terms "cup" or "acetabular cup" and the term "shell" are terms that may be used interchangeably to describe an acetabular cup component.

At the completion of step 300, the procedure advances to step 400, where a user selected head component is determined. Step 400, which similarly to step 300 is actually a procedure for determining a user selected head component, is described below in further detail in reference to FIG. 5.

At the completion of step 400, the procedure advances to step 500, where a user selected liner component is determined. Step 500, which is actually a procedure for determining a user selected stem component, is described in greater detail below in reference to FIG. 6. Note that as used herein, the terms "bearing" or "bearing insert" and the term "liner" are terms that may be used interchangeably to describe an acetabular bearing component.

At the completion of step 500, the procedure advances to step 600, where a user selected stem component is determined. Step 600, which is actually a procedure for determining a user selected stem component, is described in greater detail below in reference to FIG. 7. At the completion of step 600, the procedure advances to step 206

At step 206 the procedure generates an image of the prosthetic device selected by the user. Specifically, an image is generated which includes the user selected cup component from step 300, the user selected head component from step 400, the user selected liner component from step 500, and the user selected stem component from step 600. This image is generated as a data set which represents an image such as a bit map data set. This image is generated to simulate a view of the selected prosthetic device positioned in either the orientation selected by the user (as described below in regard to steps 700, 800) or in a default user-selected orientation. While this image is generated as a two-dimensional image, the data set from which the image is calculated represents a three-dimensional model of the prosthetic device thereby creating the illusion that the user is viewing a three-dimensional prosthetic device in three-dimensional space.

Figure 11:
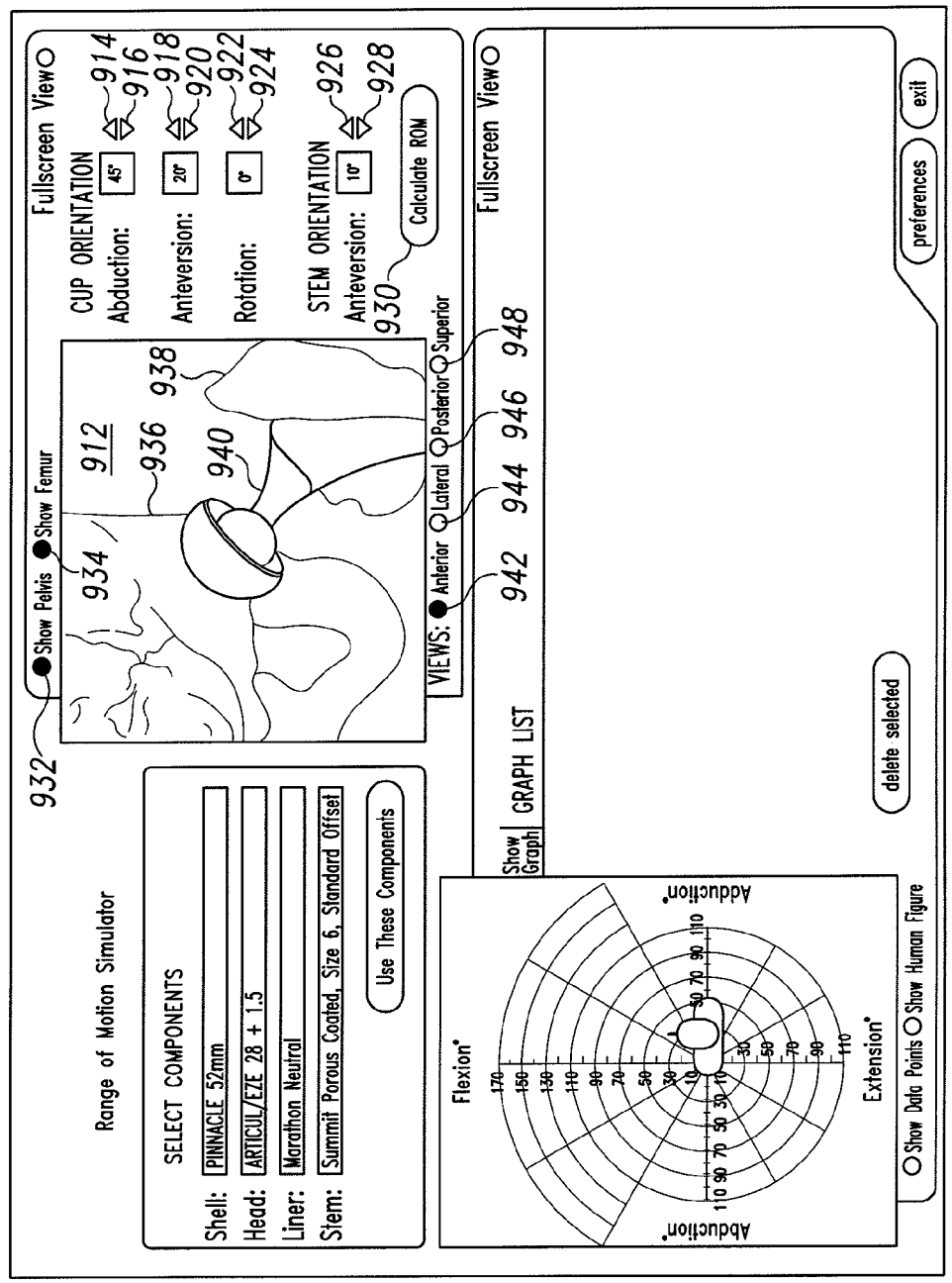
Figure 12:
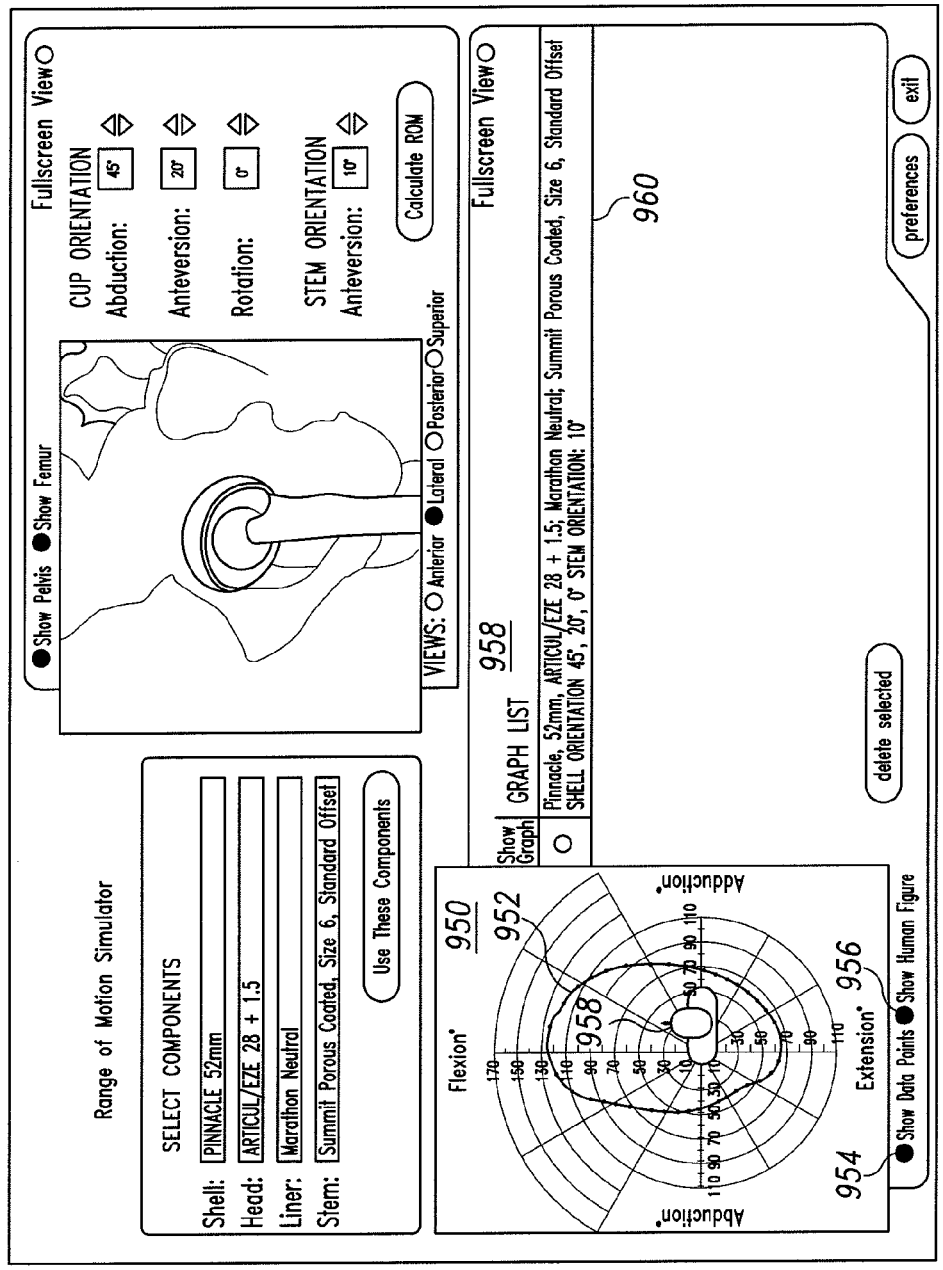

At the completion of step 206, the procedure advances to step 208, where the image generated in step 206 is displayed via the graphical user interface 900. An illustrative image 912 is shown in FIG. 11. Image 912 may include not only the selected hip prosthetic device, but also a representation of the bone structure into which a hip prosthetic device is implanted. Specifically, image 912 includes the following elements: prosthetic device 940, pelvis 932, and femur 938. The user may elect to either show or not show pelvis 936 by either selecting or deselecting show pelvis radio button 932. Similarly, the user may elect to show or not show femur 938 by selecting or deselecting show femur radio button 934. Use of an image which includes an anatomic reference (i.e., pelvis 936 and femur 938) allows the user to visualize the environment into which the selected components of prosthetic device 940 are designed to be implanted.

The user may also change image 912 to represent either an anterior, lateral, posterior, or superior view of prosthetic device 940, pelvis 936, and femur 938. This is accomplished by the selection of anterior radio button 942, lateral radio button 944, posterior radio button 946, and superior radio button 948, respectively. Upon the selection of any of the radio buttons 942, 944, 946, or 948, image 912 is regenerated based on the data set representing the prosthetic device as viewed in the selected direction, so that the desired view can be communicated to the user.

Moreover, it should be appreciated that the viewing angle of image 912 may be altered in a "free hand" manner. Specifically, user may use pointing device 108 to drag image 912 into a desired viewing angle. This feature allows for enhanced manipulation of image 912 thereby allowing a user to view the image from any one of numerous viewing angles.

Figure 8:
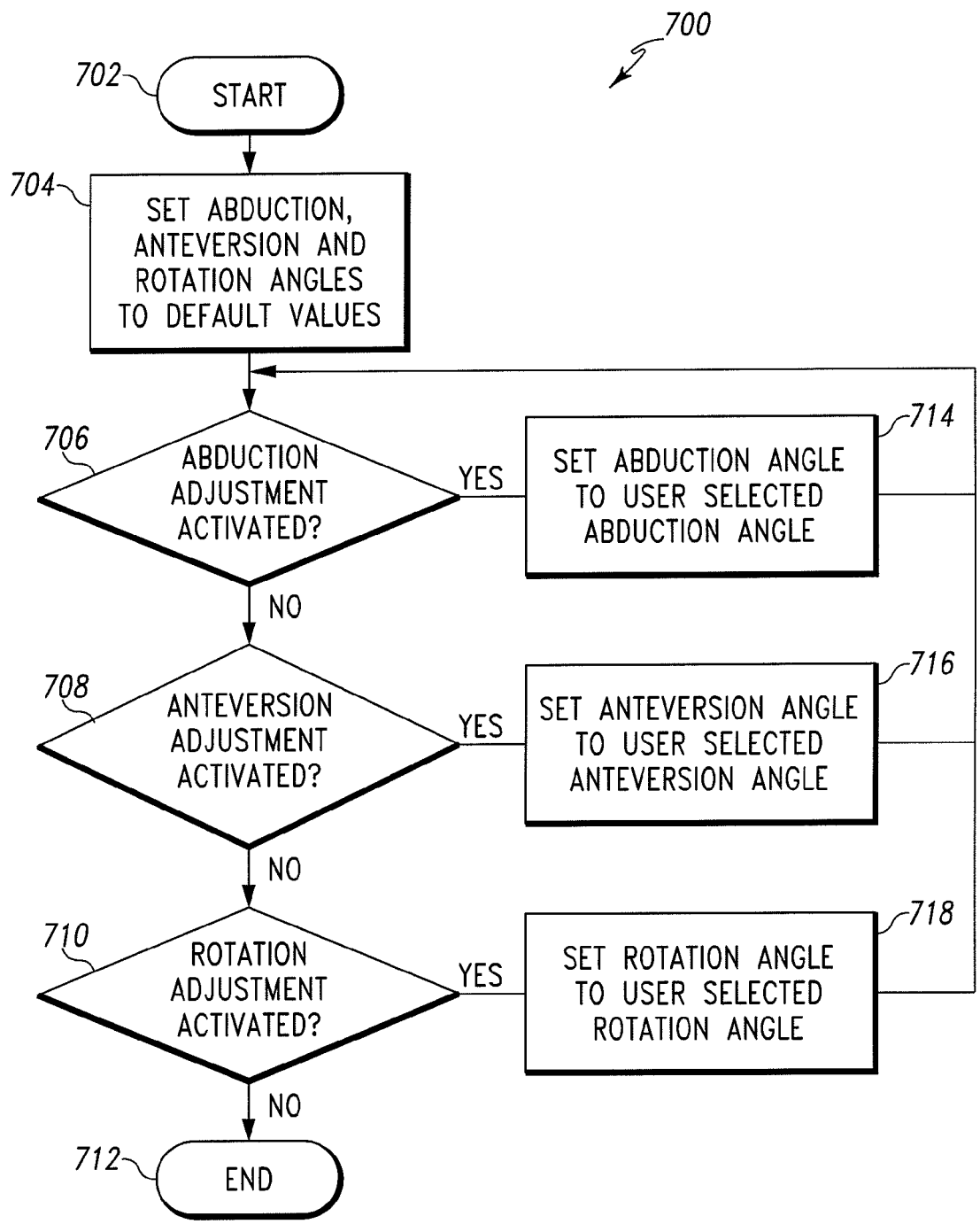
FIGS. 8 and 9 are flow charts which show in greater detail the component orientation subroutines of the procedure of FIG. 3.

At the completion of step 208 in which the image of the prosthetic device is displayed via the graphical user interface 900, the procedure 200 advances to step 700. At step 700, which is actually a sub-procedure (hereinafter also referred to with reference numeral 700), the procedure 200 determines whether the user has selected for the first time or updated a cup orientation. Specifically, as shown in FIG. 8, sub-procedure 700 begins at step 702. At the completion of start step 702, the procedure advances to step 704 at which sub-procedure 700 sets the abduction angle to the default abduction angle value, sets the anteversion angle to the default anteversion angle value, and sets the rotation angle to the default rotation angle value. As show in FIG. 11, an illustrative set of default values are as follows: an abduction angle of 45 degrees, an anteversion angle of 20 degrees, and a rotation angle of 0 degrees. At the completion of step 704, sub-procedure 700 advances to step 706.

At step 706, sub-procedure 700 determines whether an abduction adjustment has been made by the user. The user may adjust the abduction angle by activating button 914 or button 916 with pointing device 108. If the user activates button 914, the abduction angle will be increased by some amount, illustratively one degree. If the user activates button 916, the abduction angle will be decreased by some amount, illustratively one degree. If sub-procedure 700 determines that button 914 or button 916 has been activated to adjust the abduction angle, sub-procedure 700 progresses to step 714. At step 714, sub-procedure 700 sets the abduction angle to the new user selected abduction angle. At the completion of step 714, sub-procedure 700 loops back to step 706. If sub-procedure 700 determines at step 706, that the user has not activated button 914 nor button 916, then sub-procedure 700 advances to step 708.

At step 708, sub-procedure 700 determines whether an anteversion adjustment has been activated. The user may adjust the anteversion angle by activating button 918 or button 920 with pointing device 108. If the user activates button 918, the anteversion angle will be increased by some amount, illustratively one degree. If the user activates button 920, the anteversion angle will be decreased by some amount, illustratively one degree. If sub-procedure 700 determines that button 918 or button 920 has been activated to adjust the anteversion angle, sub-procedure 700 progresses to step 716. At step 716, sub-procedure 700 sets the anteversion angle to the new user selected anteversion angle. At the completion of step 716, sub-procedure 700 loops back to step 706. If sub-procedure 700 determines at step 708, that the user has not activated button 918 or button 920, then sub-procedure 700 advances to step 710.

At step 710, sub-procedure 700 determines whether an rotation adjustment has been activated. The user may adjust the rotation angle by activating button 922 or button 924 with pointing device 108. If the user activates button 922, the rotation angle will be increased by some amount, illustratively one degree. If the user activates button 924, the rotation angle will be decreased by some amount, illustratively one degree. If sub-procedure 700 determines that button 922 or button 924 has been activated to adjust the rotation angle, sub-procedure 700 progresses to step 718. At step 718, sub-procedure 700 sets the rotation angle to the new user selected rotation angle. At the completion of step 718, sub-procedure 700 loops back to step 706.

At step 712, sub-procedure 700 is complete. After the completion of step 712, image 912 of graphical user interface 900 is updated to show the new user selected cup orientation. Specifically, referring back to FIG. 3, if the sub-procedure 700 determines that any of the values associated with the cup orientation (i.e., the abduction angle, the anteversion angle, or the rotation angle) have been updated, then the procedure 200 loops back to step 206 so that a new image of the prosthetic device (positioned in its revised orientation) may be generated and thereafter displayed. However, if the procedure 200 determines that the cup orientation has not been updated, then the procedure advances to step 800.

It should be appreciated from the above discussion that because sub-procedure 700 is an endless loop, and because the procedure 200 (including sub-procedure 700) is completed in a nearly imperceptible amount of time, each activation of one of buttons 914-924 produces a change in image 912 which appears to be instantaneous to the user. For example, if the user repeatedly activates one of the buttons 914-924, image 912 will be regenerated and redisplayed so quickly that image 912 will appear to the user to be animated. In this way, the user may see an update to the cup orientation as a "real-time update", a term which for purposes of this disclosure is defined as "an update which occurs so rapidly that it appears to be instantaneous to a user".

Figure 9:
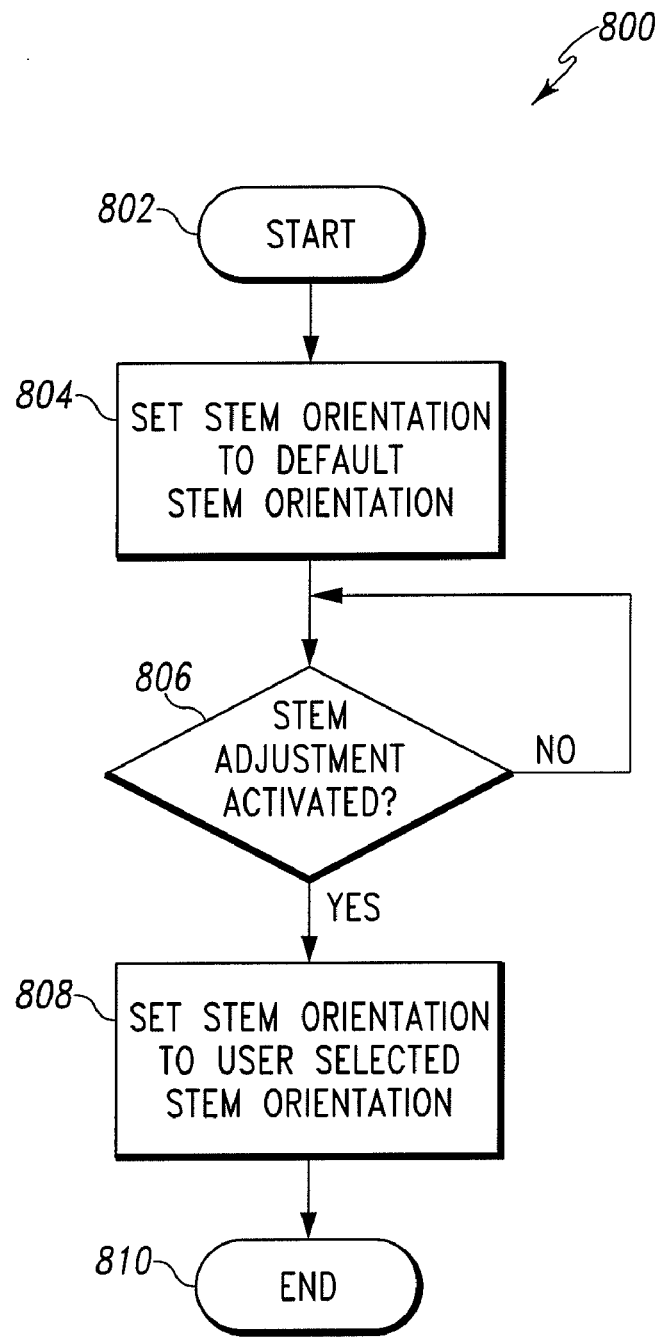

In any event, as shown in FIG. 3, at the completion of step 700, the procedure 200 advances to step 800. At step 800, which is actually a sub-procedure (hereinafter also referred to with reference numeral 800), the procedure 200 determines whether the user has selected for the first time or updated a stem orientation. Specifically, as shown in FIG. 9, sub-procedure 800 begins at step 802. At the completion of start step 802, the procedure advances to step 804. At step 804, sub-procedure 800 sets the stem orientation to the default stem orientation angle. As show in FIG. 11, an illustrative set of default stem orientation angle is ten degrees. At the completion of step 804, sub-procedure 800 advances to step 806.

At step 806, sub-procedure 800 determines whether an stem orientation adjustment has been activated. The user may adjust the stem orientation by activating button 926 or button 928 with pointing device 108. If the user activates button 926, the stem orientation will be increased by some amount, illustratively one degree. If the user activates button 928, the stem orientation will be decreased by some amount, illustratively one degree. If sub-procedure 800 determines that button 926 or button 928 has been activated to adjust the stem orientation, sub-procedure 800 progresses to step 808. At step 808, sub-procedure 800 sets the stem orientation to the new user stem orientation angle. At the completion of step 806, sub-procedure 800 advances to step 810. At step 810, sub-procedure 800 is complete. However, if sub-procedure 800 determines that neither button 926 nor button 928 have been activated by pointing device 108, procedure 800 loops back to step 806. Sub-procedure 800 will continue to loop back to step 806 awaiting activation of either button 926 or button 928 until either (i) the user actually activates button 926 or button 928 at which point procedure 800 advances to step 808 as described above, or (ii) the user selects the Calculate ROM button 930 (as described below) at which point the procedure utilizes the default stem orientation value.

After the completion of step 810, image 912 of graphical user interface 900 is updated to show the new user selected stem orientation. Specifically, referring back to FIG. 3, if the sub-procedure 800 determines that the value of the stem orientation has been updated, then the procedure 200 loops back to step 206 so that a new image of the prosthetic device (positioned in its revised orientation) may be generated and thereafter displayed. However, if the procedure 200 determines that the stem orientation has not been updated, then the procedure advances to step 214.

It should be appreciated that because sub-procedure 800 is an endless loop, and because procedure 200 (including sub-procedure 800) is completed in a nearly imperceptible amount of time, each activation of one of buttons 926, 928 produces a change in image 912 which appears to be instantaneous to the user. For example, if the user repeatedly activates one of the buttons 926, 928, image 912 will be regenerated and redisplayed so quickly that image 912 will appear to the user to be animated. In this way, the user may see an update to the stem orientation as a real-time update.

Once the user has selected a desired cup orientation and a desired stem orientation (or chosen a default setting), and an image of the hip prosthetic device positioned in an orientation consistent with such selections has been displayed to the user, the procedure 200 advances to step 214 (see FIG. 3) to monitor the user's activation of the Calculate ROM button 930. Specifically, at step 214 the procedure determines whether the user has requested a range of motion graph. The user may request a range of motion graph by activating a calculate ROM button 930 of graphical user interface 900, as shown in FIG. 11. If the user has not requested a range of motion graph, the procedure returns to step 206 and continues in a loop to determine whether either the cup orientation or the stem orientation have been updated, or whether a range of motion graph has been requested. However, if the procedure determines at step 214 that the user has requested a range of motion graph, then the procedure advances to step 216.

Figure 13:
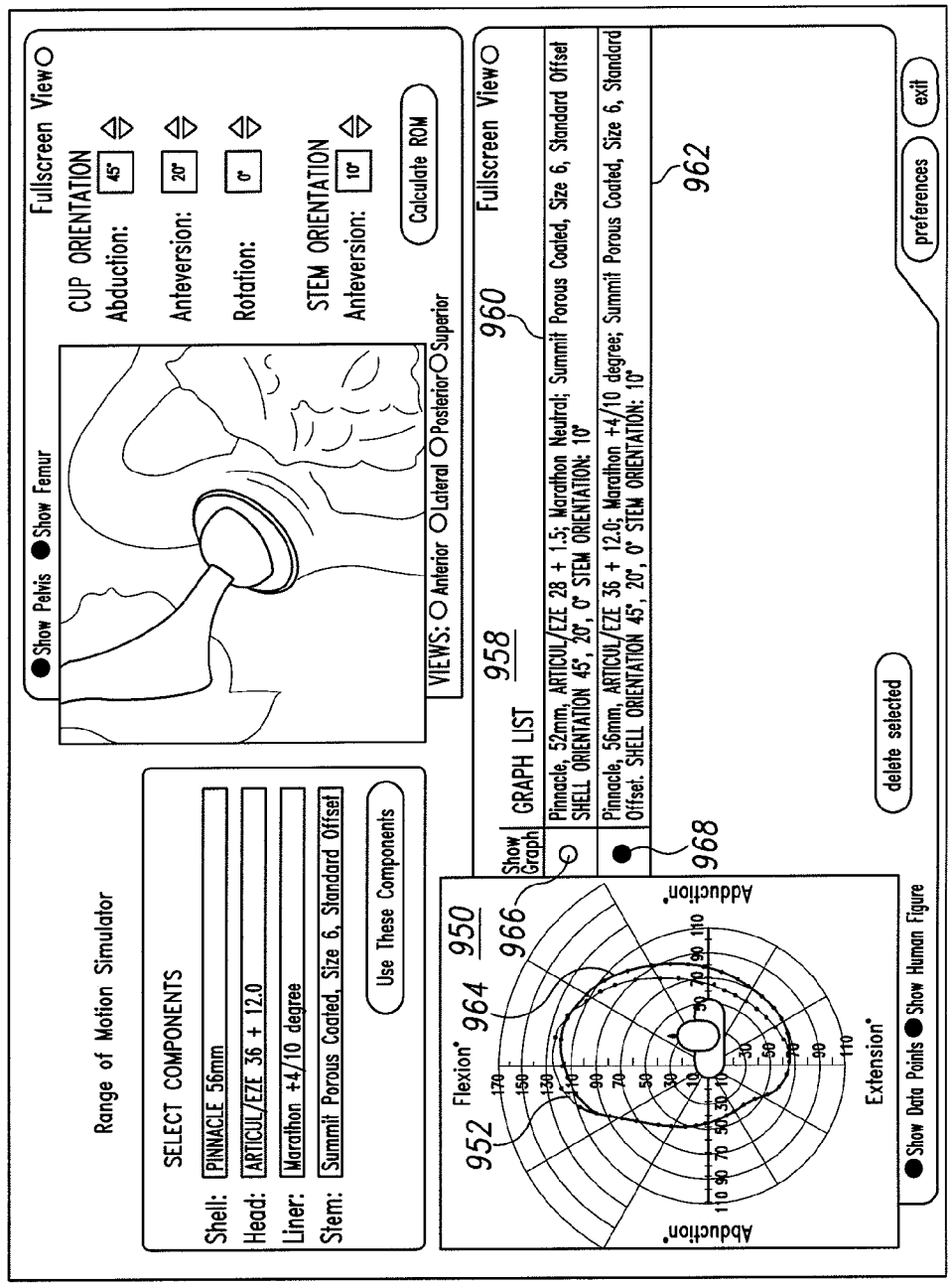

At step 216, the procedure displays a graph of the range of motion for a hip joint having implanted therein the user-selected prosthetic device positioned in the user-selected orientation. An illustrative range of motion graph 950 is shown in FIGS. 12-15. Graph 950 includes two axes with the X-axis representing degrees of abduction in the negative direction and degrees of adduction in the positive direction, and the Y-axis representing degrees of flexion in the positive direction and degrees of extension in the negative direction. The origin represents the location of the hip prosthetic device. As shown in FIG. 13, a range of motion plot 952 is calculated as a series of points, which are linked together by a series of line segments. A collision algorithm is used to calculate each of the points in the series, as is well-known in the art. The user may elect to either show or not show human Figure 948 by either selecting or deselecting show human figure radio button 956. Likewise, the user may elect to either show or not to show the actual data points by either selecting or deselecting show data points ratio button 954.

At the completion of step 216, the procedure proceeds to end step 218. However, once the procedure has ended, the procedure returns to start step 202. At this point, the user may select a second prosthetic device, having a second orientation. The user selects this second prosthetic device and second orientation in the same manner that the user selected the first prosthetic device and first orientation. During this second selection process, range of motion plot 952 will continue to be displayed. Furthermore, graph list 958 will include plot entry 960 (which is indicative of the configuration of the first selected prosthetic device and the first selected orientation) throughout this second device selection and orientation process. After the user has completed steps 204-800 for the second iteration, the procedure will advance to step 214 to determine whether the user has requested a second range of motion plot.

Similarly to as described above, the user requests a range of motion graph by selecting calculate ROM button 930 of the graphical user interface 900. After the user requests a second range of motion plot, the procedure advances to step 216, and displays a second range of motion plot for the second prosthetic device, via the graphic user interface 900. At step 216, graph 950 is updated to further include range of motion plot 964, and graph list 958 is updated to include second range of motion plot entry 962, as shown in FIG. 13.

As can be seen in FIG. 13, the simultaneous display of range of motion plot 952 and range of motion plot 964 allows the user to analyze the effects of various component selections and various component orientations on the range of motion. Graph list 958 includes a show plot radio button 966 and plot radio button 968. The user may elect to display or not display range of motion plot 952 by either selecting or deselecting show plot radio button 966. Similarly, the user may elect to display or not to display range of motion plot 964 by either selecting or deselecting show plot radio 968.

Figure 14:
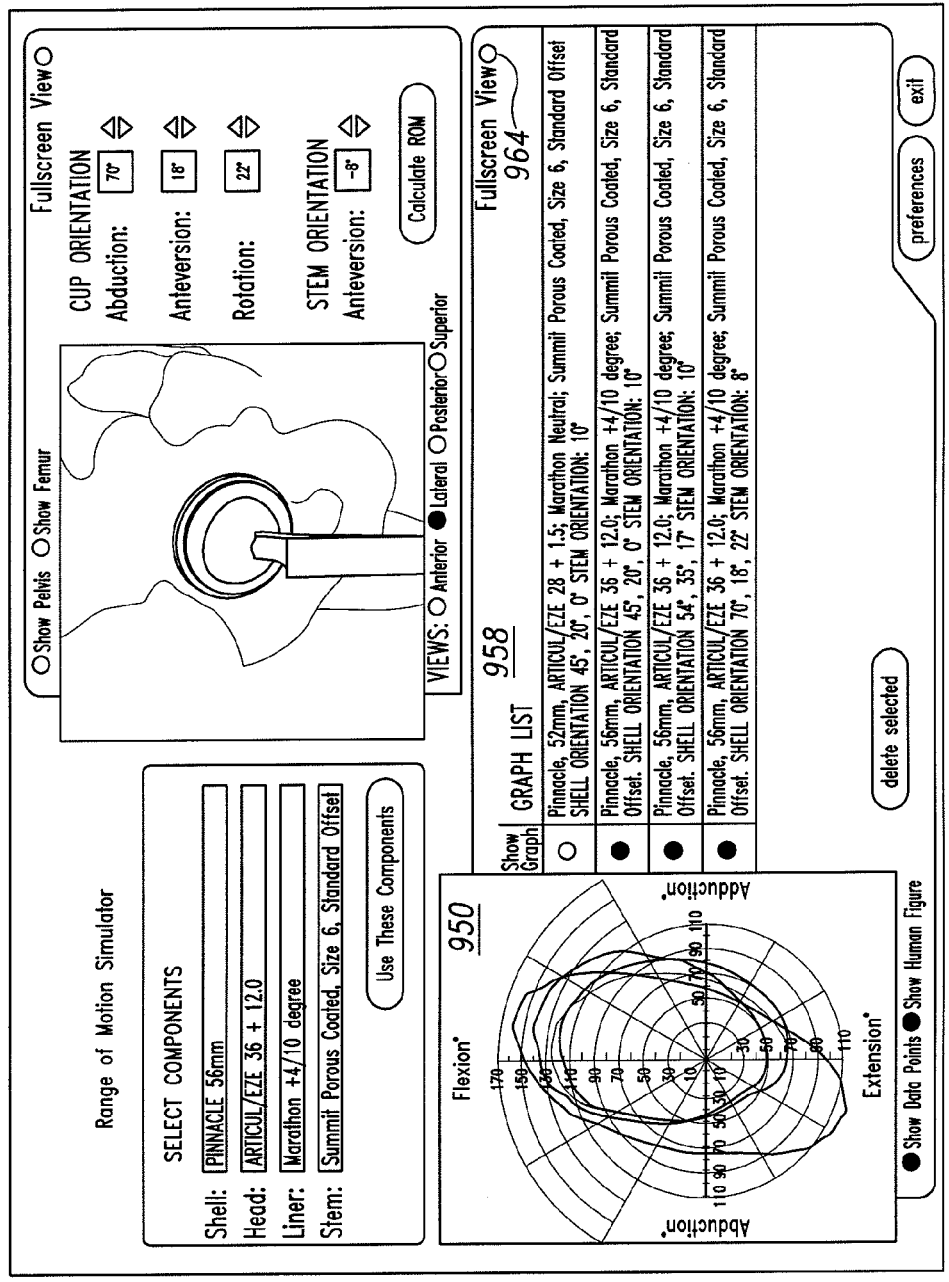

The ability to turn each range of motion plot "on" or "off" is helpful because the user may execute procedure 200 multiple times, in which case a multiplicity of plots may be displayed simultaneously in graph 950. As one illustrative example, FIG. 14 illustrates graph 950 simultaneously displaying four individual range of motion plots. As can be seen in this illustrative example, simultaneously viewing a multiplicity of plots allows for a comparative analysis of the individual plots relative to one another. However, as graph list 958 includes a show plot radio button for each range of motion plot, the user may "turn on" or "turn off" each plot in order to make desired comparisons of any one or more of the plots.

Figure 15:
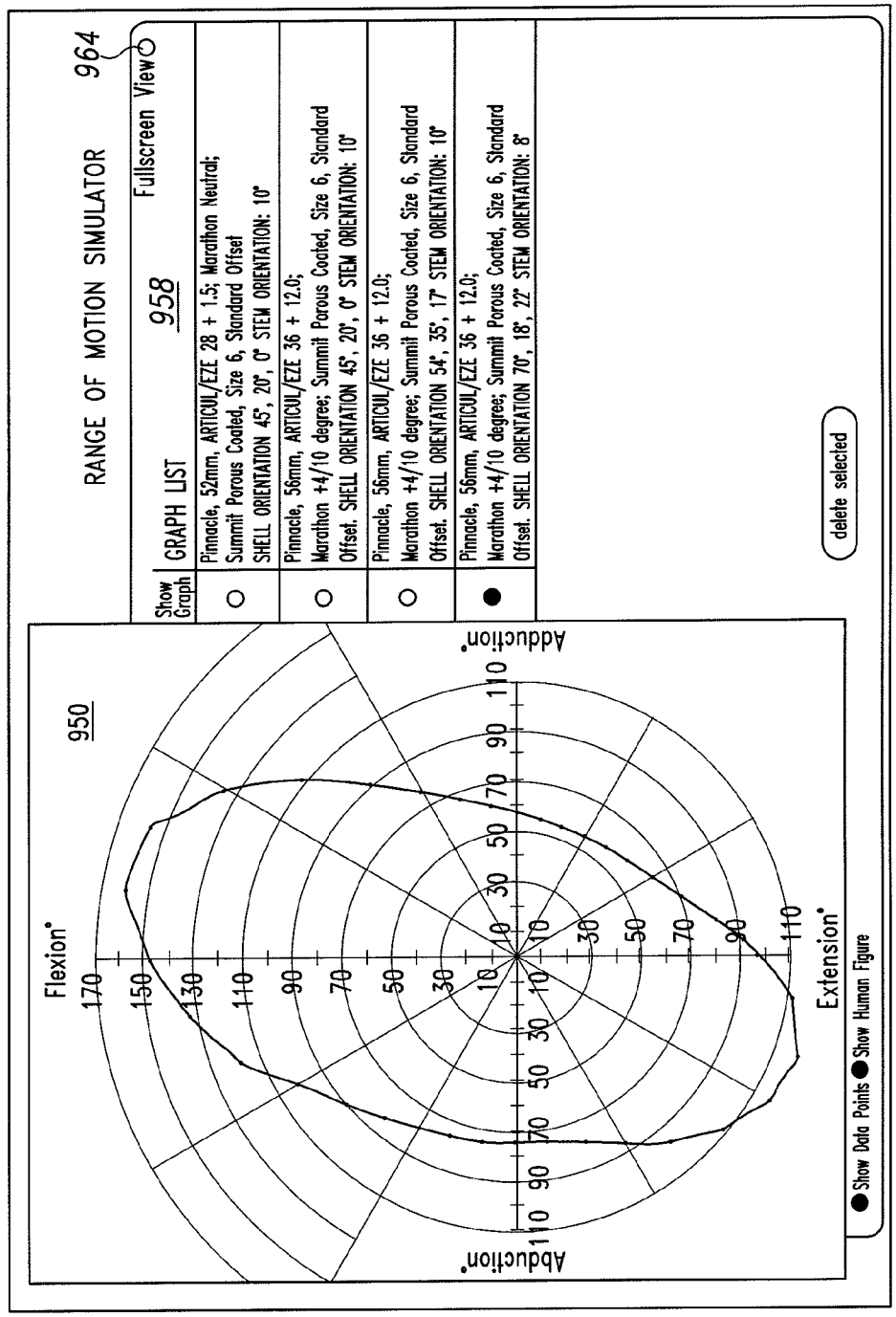

Another feature of procedure 200 which is provided in order to aid the user in analysis is a full screen graph viewing mode. The full screen graph viewing mode allows the user to enlarge graph 950 so that graph 950 and graph list 958 utilize substantially the entire viewing area of monitor 102 of computer system 100. The user selects full screen graph viewing mode by activating a full screen view radio button 964. Upon this activation, procedure 200 responds by changing graphical user interface 900 to display only graph 950 and graph list 958, as shown in FIG. 15. As illustrated in FIG. 15, four plots are available for viewing in graph list 958, however, only one plot is actually selected for viewing, and therefore only one plot is displayed in graph 950.

In order for the user to return to a graphical user interface including the component selection section and prosthetic device image 912, the user again selects (i.e., "de-selects") full screen view radio button 964. It will be understood by those skilled in the art that the procedure described herein provides a user with a quick and intuitive comparative assessment of the range of motion for various component selections and orientations of a prosthetic device. It will be further understood by those skilled in the art that the steps and order of procedure 200 may be varied without departing from the scope of the disclosure as claimed herein.

Figure 4:
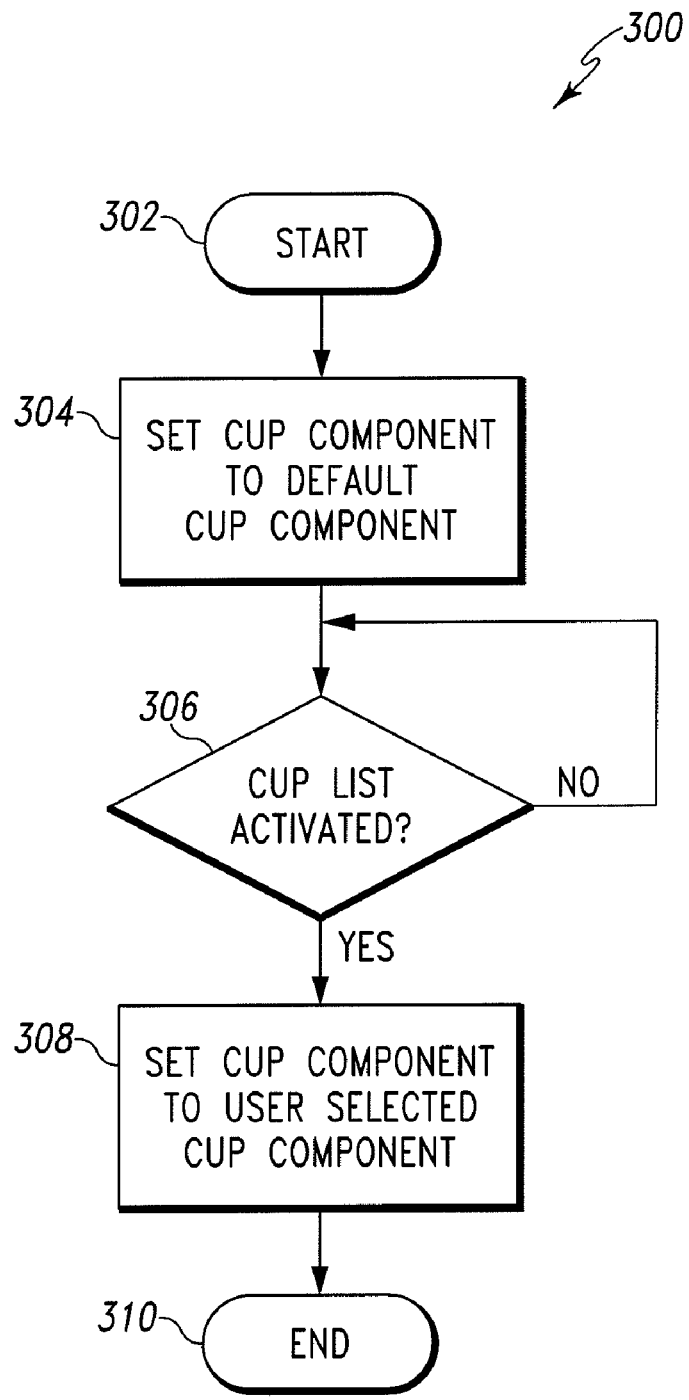
FIGS. 4-7 are flow charts which show in greater detail the component selection subroutines of the procedure of FIG. 3.

Turning now to FIG. 4, step 300 for determining a user selected cup component will be described in greater detail. As explained above, when general procedure 200 completes step 204 in which the graphical user interface 900 is displayed, general procedure 200 progresses to step 300. Procedure 300 begins at step 302, the start step. At the completion of step 302, procedure 300 advances to step 304 in which procedure 300 sets the cup component to the default cup component.

Turning to FIG. 10, a drop down list 902 containing available acetabular cup components (as indicated by the title "Shell") is shown. List 902 is activated by the user's operation of pointing device 108. Such use of pointing devices to activate drop down lists in graphical user interfaces is well known in the art. In the illustrative embodiment illustrated in FIG. 10, list 902 has been set to a default cup component described as "Pinnacle, 52 MM", however any cup component could be used as the default cup component.

Procedure 300 then advances to step 306. At step 306, procedure 300 determines whether the user has "opened" or otherwise activated list 902 via pointing device 108. If list 902 has been activated by pointing device 108, procedure 300 progresses to step 308. However, if list 902 has not been activated by pointing device 108, procedure 300 loops back to step 306. Procedure 300 will continue to loop back to step 306 awaiting activation of list 902 until either (i) the user actually activates list 902 at which point procedure 300 advances to step 308, or (ii) the user selects the use these components button 910 (as described below) at which point the procedure utilizes the default cup component.

At step 308, procedure 300 determines which cup component was selected by the user from list 902, and sets the current cup component to the user selected cup component. At the completion of step 308, procedure 300 advances to step 310, and ends. Procedure 300 then returns to start step 302 if a user repeats the cup selection process.

Figure 5:
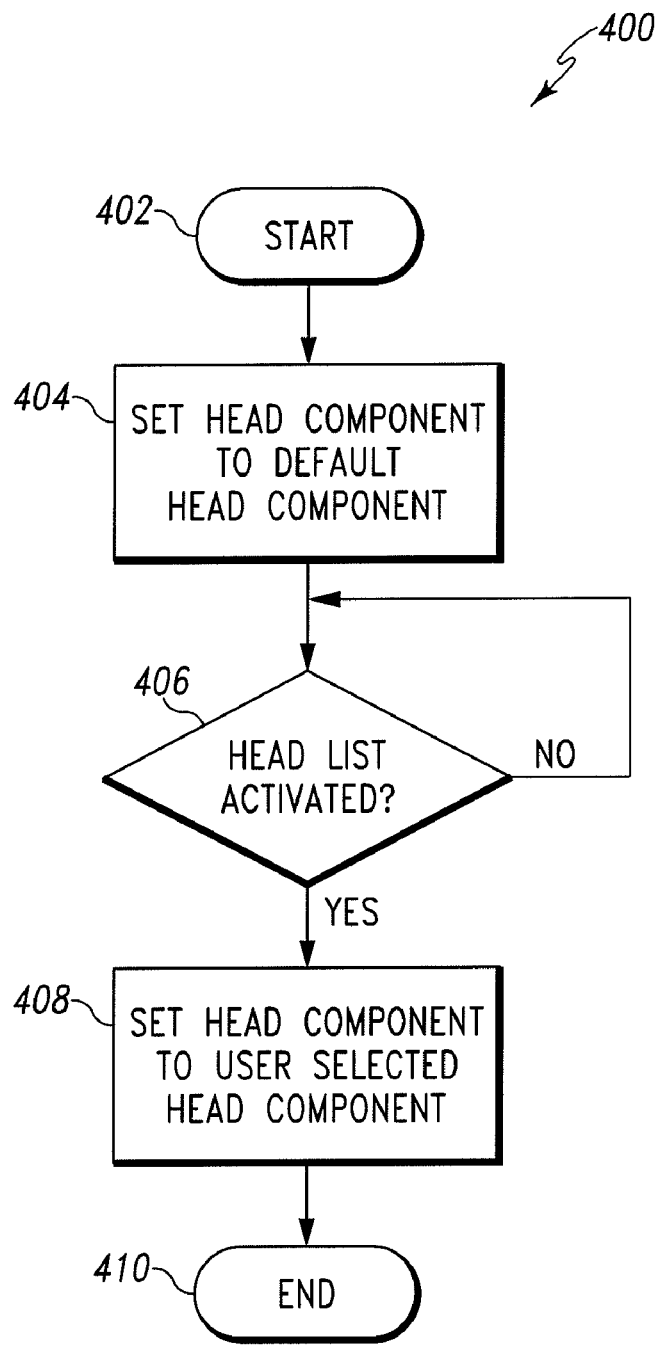

Turning now to FIG. 5, step 400 for determining a user selected head component will be described in further detail. As explained above, when general procedure 200 completes step 300, general procedure 200 progresses to step 400. Procedure 400 begins at step 402, the start step. At the completion of step 402, procedure 400 advances to step 404 in which procedure 400 sets the head component to the default head component.

Turning to FIG. 10, a drop down list 904 containing available head components is shown. List 904 is also activated by a user's use of pointing device 108. In the illustrative embodiment illustrated in FIG. 10, list 904 has been set to a default head component described as "ARTICUL/EZE 28+1.5", however any head component could be used as the default head component.

Procedure 400 then advances to step 406. At step 406, procedure 400 determines whether list 904 has been "opened" or otherwise activated via pointing device 108. If list 904 has been activated by pointing device 108, procedure 400 progresses to step 408. However, if list 904 has not been activated by pointing device 108, procedure 400 loops back to step 406. Procedure 400 will continue to loop back to step 406 awaiting activation of list 904 until either (i) the user actually activates list 904 at which point procedure 400 advances to step 408, or (ii) the user selects the use these components button 910 (as described below) at which point the procedure utilizes the default head component.

At step 408, procedure 400 determines which head component was selected by the user from list 904, and sets the current head component to the user selected head component. At the completion of step 408, procedure 400 advances to step 410, and ends. Procedure 400 then returns to start step 402 if the user repeats the head selection process.

Figure 6:
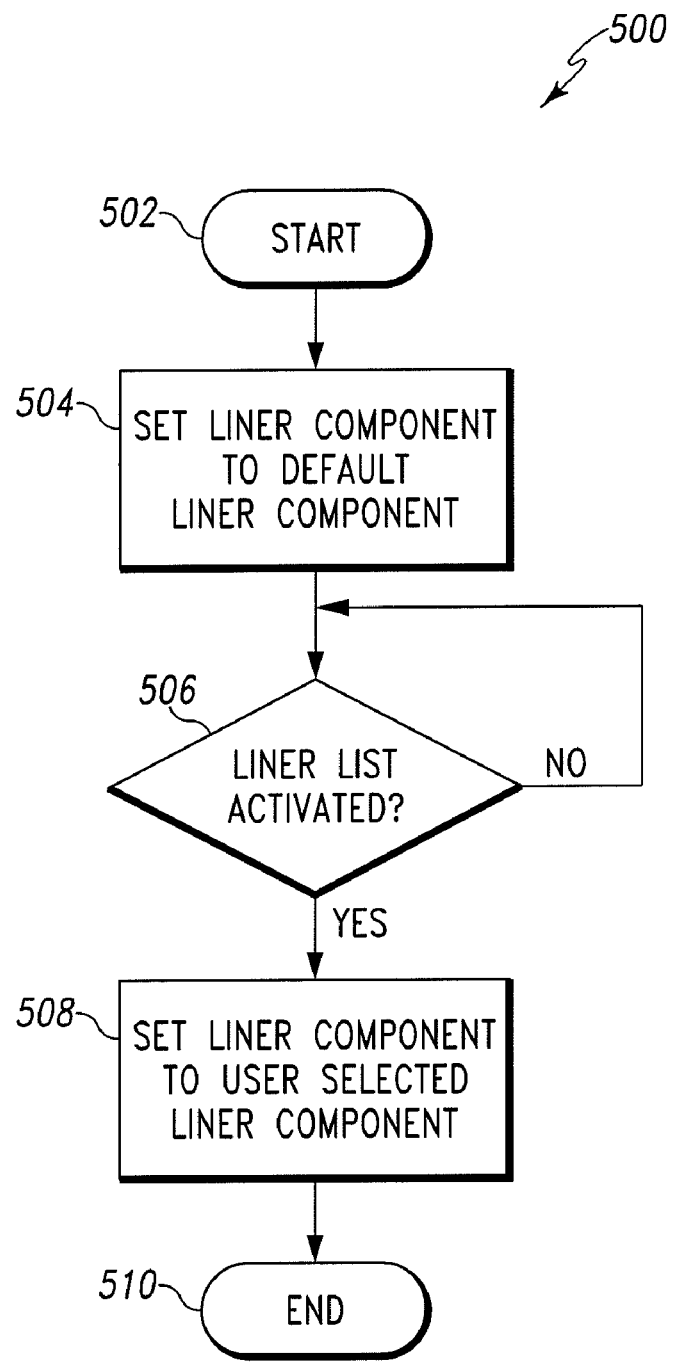

Turning now to FIG. 6, step 500 for determining a user selected liner component will be described in further detail. As explained above, when general procedure 200 completes step 400, general procedure 200 progresses to step 500. Procedure 500 begins at step 502, the start step. At the completion of step 502, procedure 500 advances to step 504 in which procedure 500 sets the liner component to the default liner component.

Turning again to FIG. 10, a drop down list 906 containing available liner components is shown. As with the previously described lists, list 906 is activated by pointing device 108. In the illustrative embodiment illustrated in FIG. 10, list 906 has been set to a default liner component described as "Marathon Neutral", however any liner component could be used as the default liner component.

Procedure 500 then advances to step 506. At step 506, procedure 500 determines whether list 906 has been "opened" or otherwise activated via pointing device 108. If list 906 has been activated by pointing device 108, procedure 500 progresses to step 508. However, if list 906 has not been activated by pointing device 108, procedure 500 loops back to step 506. Procedure 500 will continue to loop back to step 506 awaiting activation of list 906 until either (i) the user actually activates list 906 at which point procedure 500 advances to step 508, or (ii) the user selects the use these components button 910 (as described below) at which point the procedure utilizes the default liner component.

At step 508, procedure 500 determines which liner component was selected by the user from list 906, and sets the current liner component to the user selected liner component. At the completion of step 508, procedure 500 advances to step 510, and ends. Procedure 500 then returns to start step 502 if the user repeats the liner selection process.

Figure 7:
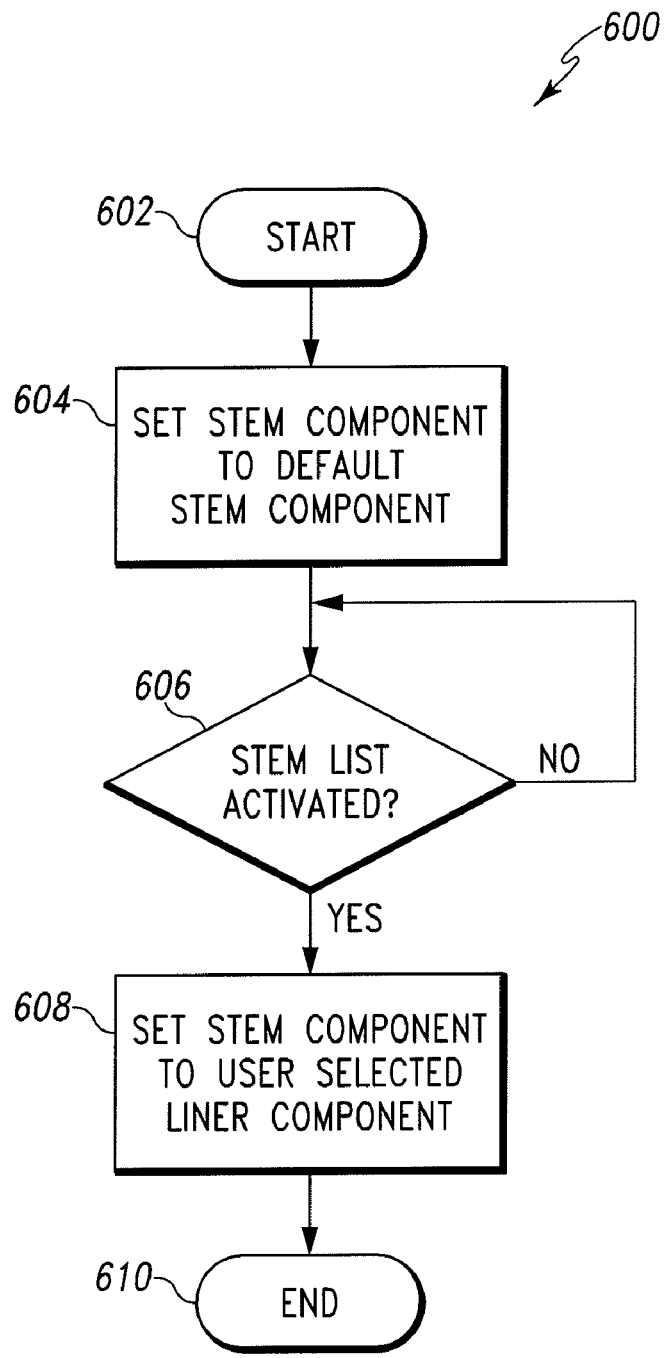

Turning now to FIG. 7, step 600 for determining a user selected stem component will be described in further detail. As explained above, when general procedure 200 completes step 500, general procedure 200 progresses to step 600. Procedure 600 begins at step 602, the start step. At the completion of step 602, procedure 600 advances to step 604 in which procedure 600 sets the stem component to the default stem component.

Referring again to FIG. 10, a drop down list 908 containing available stem components is shown. Similarly to the lists described above, list 906 is activated by pointing device 108. In the illustrative embodiment illustrated in FIG. 10, list 908 has been set to a default stem component described as "Summit Porous Coated, Size 6, Standard Offset", however any stem component could be used as the default stem component.

At the completion of step 604, procedure 600 advances to step 606. At step 606, procedure 600 determines whether list 906 has been "opened" or otherwise activated via pointing device 108. If list 908 has been activated by pointing device 108, procedure 600 progresses to step 608. However, if list 908 has not been activated by pointing device 108, procedure 600 loops back to step 606. Procedure 600 will continue to loop back to step 606 awaiting activation of list 908 until either (i) the user actually activates list 908 at which point procedure 600 advances to step 608, or (ii) the user selects the use these components button 910 (as described below) at which point the procedure utilizes the default stem component.

At step 608, procedure 600 determines which stem component was selected by the user from list 908, and sets the current stem component to the user selected stem component. At the completion of step 608, procedure 600 advances to step 610, and ends. Procedure 600 then returns to start step 602 if the user repeats the stem selection process.

At the completion of procedure 600, either the user has selected a cup component, a head component, a liner component, and a stem component, or a default value has remained for one or more of the components. Such default values effectively become the user selection for the one or more components which were not specifically selected by the user. Activation of use these components button 910 indicates to general procedure 200 at step 206 that the components currently set as user selected components (including any default selections) define the hip prosthetic device for use in the remaining steps of procedure 200. Therefore, at step 206, the image that is generated is that of a hip prosthetic device that includes these user selected components (including any default selections). Furthermore, image 912 which is displayed in graphical user interface 900 in step 208 is an image of a hip prosthetic device having the user selected components.

While the apparatus, methods, and programs disclosed herein are susceptible to various modifications and alternative forms, specific embodiments thereof have been described by way of example herein. Many modifications may be made to the disclosed apparatus, methods, and programs without departing from the scope of the invention claimed herein. For example, the selection of components via graphical user interface 900 could be performed by the use of other input devices in lieu of pointing device 108. For example, the selection of components via graphical user interface 900 could be performed by the use of keyboard 106 or a voice recognition system (not shown) attached to computer system 100. For further example, graphical user interface 900 could be displayed on a head-mounted binocular "virtual reality" display system in lieu of display monitor 102, in which case two images would be generated to provide a truly thee-dimensional view.

It will be apparent to those skilled in the art that these and many other variations may be easily made without departing from the invention claimed herein. It should be further understood that there is no intent to limit the invention to the particular forms disclosed, but on the contrary, the intention is to cover all modifications, equivalents, and alternatives falling within the spirit and scope of the invention as defined in the appended claims.

The invention claimed is:

1. A method for analyzing a prosthetic device, the method comprising the steps of:
   displaying a graphical user interface;
   displaying a first list of prosthetic components via the graphical user interface;
   determining a first user selected prosthetic component from the first list, the prosthetic device comprising the first user selected prosthetic component;
   displaying an image of the prosthetic device via the graphical user interface;
   determining a first user selected orientation for the prosthetic device via the graphical user interface;
   calculating a first data set indicative of a first range of motion for the prosthetic device orientated in the first user selected orientation; and
   displaying a graphical representation of the first data set via the graphical user interface.

2. The method of claim 1, further comprising displaying a second list of prosthetic components via the graphical user interface, and determining a second user selected prosthetic component from the second list, the prosthetic device further comprising the second user selected prosthetic component.

3. The method of claim 2, further comprising displaying a third list of prosthetic components via the graphical user interface, and determining a third user selected prosthetic component from the third list, the prosthetic device further comprising the third user selected prosthetic component.

4. The method of claim 3, further comprising displaying a fourth list of prosthetic components via the graphical user interface, and determining a fourth user selected prosthetic component from the fourth list, the prosthetic device further comprising the fourth user selected prosthetic component.

5. The method of claim 4, wherein the prosthetic device is a hip replacement system, the first user selected prosthetic component is an acetabular cup component the second user selected prosthetic component is a femoral head component, the third user selected prosthetic component is a liner component, and the fourth user selected prosthetic component is a stem component.

6. The method of claim 4, wherein the step of determining the first user selected prosthetic component further includes determining that a default first component is the user selected first component until a user selects another first component from the first list, determining the second user selected prosthetic component further includes determining that a default second component is the user selected second component until a user selects another second component from the second list, determining the third user selected prosthetic component further includes determining that a default third component is the user selected third component until a user selects another third component from the third list, and determining the fourth user selected prosthetic component further includes determining that a default fourth component is the user selected fourth component until a user selects another fourth component from the fourth list.

7. The method of claim 1, wherein the step of determining a first user selected orientation for the prosthetic device via the graphical user interface includes determining a first user selected cup orientation.

8. The method of claim 7, wherein the step of determining a first user selected cup orientation includes detennining a first user selected cup abduction angle.

9. The method of claim 7, wherein the step of determining a first user selected cup orientation includes determining a first user selected cup anteversion angle.

10. The method of claim 7, wherein the step of determining a first user selected cup orientation includes determining a first user selected cup rotation angle.

11. The method of claim 1, wherein the step of determining a first user selected orientation for the prosthetic device via the graphical user interface includes determining a first user selected stem orientation for the prosthetic device.

12. The method of claim 1, wherein the step of deteterming a first user selected orientation for the prosthetic device via the graphical user interface includes determining a first user selected stem orientation and a first user selected cup orientation.

13. The method of claim 12, wherein the step of displaying an image of the prosthetic device via the graphical user interface includes generating the image of the prosthetic device based upon the user selected cup orientation and the user selected stem orientation.

14. The method of claim 13, wherein the step of displaying an image of the prosthetic device via the graphical user interface further includes determining a second user selected orientation for the prosthetic device via the graphical user interface, generating a second image of the prosthetic device based upon second user selected orientation for the prosthetic device, and displaying the second image of the prosthetic device via the graphical user interface.

15. The method of claim 1, wherein the step of displaying an image of the prosthetic device via the graphical user interface includes displaying the image of the prosthetic device relative to an image of a bone.

16. The method of claim 1, wherein the step of displaying an image of the prosthetic device via the graphical user interface further includes generating the image of the prosthetic device based upon the user selected cup orientation and the user selected stem orientation, and displaying the image of the prosthetic device relative to the image of a bone.

17. The method of claim 16, wherein the step of displaying an image of the prosthetic device via the graphical user interface further includes detennining a second user selected orientation for the prosthetic device via the graphical user interface, generating a second image of the prosthetic device based upon second user selected orientation for the prosthetic device, and displaying the second image of the prosthetic device via the graphical user interface relative to the image of a bone.

18. The method of claim 1, further including the steps of determining a second user selected orientation for the prosthetic device via the graphical user interface, calculating a second data set indicative of a second range of motion for the prosthetic device orientated in the second user selected orientation, and displaying a graphical representation of the second data set via the graphical user interface.

19. The method of claim 18, wherein the step of displaying a graphical representation of the second data set via the graphical user interface includes simultaneously displaying the graphical representation of the first data set.

20. A method for analyzing a prosthetic device, the method comprising the steps of:
    displaying a graphical user interface on a first computer;
    displaying a list of prosthetic components via the graphical user interface;
    determining a user selected prosthetic component from the list; the prosthetic device comprising the user selected prosthetic component;
    displaying an image of the prosthetic device via the graphical user interface;
    determining a user selected orientation for the prosthetic device via the graphical user interface;
    calculating a data set indicative of a first range of motion for the prosthetic device, the calculation based upon the user selected orientation for the prosthetic device, the calculation performed by a second computer; and
    displaying a graphical representation of the data set via the graphical user interface.

21. The method of claim 20, further including the steps of transmitting data indicating the user selected prosthetic device from the first computer to the second computer via a network, generating the image of the prosthetic device with the second computer, and transmitting the image of the prosthetic device from the second computer to the first computer via the network.

22. The method of claim 20, further including the steps of transmitting data indicating the user selected orientation for the prosthetic device from the first computer to the second computer via a network and transmitting the data set indicative of a range of motion for the prosthetic device from the second computer to the first computer via the network.

23. The method of claim 20, wherein the step of displaying a graphical user interface on a first computer includes utilizing a hypertext mark-up language capable computer program to display text and graphics on a computer display.

24. The method of claim 20, wherein the step of determining a user selected prosthetic device via the graphical user interface includes utilizing a hypertext mark-up language capable computer program to receive input from a computer pointing device, and wherein the step of determining a user selected orientation for the prosthetic device via the graphical user interface includes utilizing the computer program to receive input from the computer pointing device.

25. An apparatus for analyzing a prosthetic device, the apparatus comprising:
    a display monitor;
    a processing unit electrically coupled to the display monitor;
    a memory electrically coupled to the processing unit, the memory having stored therein a plurality of instructions which, when executed by the processing unit, causes the processing unit to:
    display a graphical user interface on the display monitor;
    display a first list of prosthetic components on the display monitor;
    determine a first user selected prosthetic component from the first list, the prosthetic device comprising the first user selected prosthetic component;
    display an image of the prosthetic device via the graphical user interface;
    determine a first user selected orientation for the prosthetic device via the graphical user interface;
    calculate a first data set indicative of a first range of motion for the prosthetic device orientated in the first user selected orientation; and
    display a graphical representation of the first data set via the graphical user interface.

26. The apparatus of claim 25, wherein the plurality of instructions, when executed by the processing unit, further causes the processing unit to:
    display a second list of prosthetic components on the display monitor, and
    determine a second user selected prosthetic component from the second list, the prosthetic device further comprising the second user selected prosthetic component.

27. The apparatus of claim 26, wherein the plurality of instructions, when executed by the processing unit, further causes the processing unit to:
    display a third list of prosthetic components on the display monitor, and
    determine a third user selected prosthetic component from the third list, the prosthetic device further comprising the third user selected prosthetic component.

28. The apparatus of claim 27, wherein the plurality of instructions, when executed by the processing unit, further causes the processing unit to:
    display a fourth list of prosthetic components on the display monitor, and
    determine a fourth user selected prosthetic component from the fourth list, the prosthetic device further comprising the fourth user selected prosthetic component.

29. The apparatus of claim 28, wherein the prosthetic device is a hip replacement system, the first user selected prosthetic component is an acetabular cup component, the second user selected prosthetic component is a femoral head component, the third user selected prosthetic component is a liner component, and the fourth user selected prosthetic component is a stem component.

30. An article comprising:
    a computer-readable data storage medium, the medium having recorded thereon a plurality of instructions which, when executed by a processing unit, causes the processing unit to:
    generate a graphical user interface for display on a display monitor;
    generate a first list of prosthetic components of a prosthetic device for display on the display monitor;
    determine a first user selected prosthetic component from the first list, the prosthetic device comprising the first user selected prosthetic component;
    generate an image of the prosthetic device for display on the display monitor via the graphical user interface;
    determine a first user selected orientation for the prosthetic device via the graphical user interface;
    calculate a first data set indicative of a first range of motion for the prosthetic device orientated in the first user selected orientation; and generate a graphical representation of the first data set for display on the display monitor via the graphical user interface.

31. The article of claim 30, wherein the plurality of instructions, when executed by the processing unit, further causes the processing unit to:
generate a second list of prosthetic components for display on the display monitor, and
determine a second user selected prosthetic component from the second list, the prosthetic device further comprising the second user selected prosthetic component.

32. The article of claim 31, wherein the plurality of instructions, when executed by the processing unit, further causes the processing unit to:
generate a third list of prosthetic components for display on the display monitor, and
determine a third user selected prosthetic component from the third list, the prosthetic device further comprising the third user selected prosthetic component.

33. The article of claim 32, wherein the plurality of instructions, when executed by the processing unit, further causes the processing unit to:
generate a fourth list of prosthetic components for display on the display monitor, and
determine a fourth user selected prosthetic component from the fourth list, the prosthetic device further comprising the fourth user selected prosthetic component.

34. The apparatus of claim 33, wherein the prosthetic device is a hip replacement system, the first user selected prosthetic component is an acetabular cup component, the second user selected prosthetic component is a femoral head component, the third user selected prosthetic component is a liner component, and the fourth user selected prosthetic component is a stem component.

* * * * *